US005190031A

United States Patent [19]
Guibert et al.

[11] Patent Number: 5,190,031
[45] Date of Patent: * Mar. 2, 1993

[54] UNIVERSAL THERMOTHERAPY APPLICATOR

[76] Inventors: Raul Guibert; Bettina Guibert, both of 2800 Plaza del Amo #418, Torrance, Calif. 90503

[*] Notice: The portion of the term of this patent subsequent to Apr. 28, 2009 has been disclaimed.

[21] Appl. No.: 829,232

[22] Filed: Feb. 3, 1992

Related U.S. Application Data

[63] Continuation of Ser. No. 667,186, Mar. 11, 1991, Pat. No. 5,107,832.

[51] Int. Cl.$^5$ ................................................ A61F 7/00
[52] U.S. Cl. ..................................................... 128/399
[58] Field of Search ............... 128/399, 400, 401, 362; 34/100; 219/400

[56] References Cited

U.S. PATENT DOCUMENTS

| Re. 19,724 | 10/1935 | Martin | 128/362 |
|---|---|---|---|
| 1,903,427 | 6/1930 | Martin | 128/400 |
| 2,062,992 | 1/1936 | Martin | 34/100 |
| 2,133,078 | 10/1938 | Carter | 34/100 |
| 2,197,752 | 8/1938 | Kallmann | 34/100 |
| 2,232,156 | 2/1941 | Abeles | 128/399 |
| 2,334,056 | 11/1943 | Anderson | 219/400 |
| 2,542,699 | 2/1951 | Oliver | 219/400 |
| 3,082,540 | 3/1963 | Hiltenbrand | 34/100 |
| 3,516,411 | 5/1968 | Adler | 128/399 |
| 3,816,940 | 6/1974 | Cournoyer | 34/100 |
| 4,398,535 | 8/1983 | Guibert | 128/399 |
| 4,595,008 | 6/1986 | Guibert | 128/399 |
| 4,667,658 | 5/1987 | Guibert | 128/400 |
| 4,671,788 | 1/1987 | Wu | 128/399 |
| 5,107,832 | 4/1992 | Guibert et al. | 128/399 |

Primary Examiner—William H. Grieb
Attorney, Agent, or Firm—Michael Ebert

[57] ABSTRACT

A universal applicator for applying therapeutic heat to a localized skin area of a patient. The applicator includes a casing dome whose open base is maintained in spaced relation to the skin area to define an air flow zone therebetween. Coaxially mounted at an intermediate position within the dome is a motor-driven fan which creates a negative pressure region in the dome above the fan and a positive pressure region therebelow, whereby air drawn from the negative pressure region is propelled into the positive pressure region from which it is discharged into the air flow zone. From this zone, the air is returned to the negative pressure region, thereby creating a circulatory flow loop minimizing the discharge of air into the atmosphere outside the flow zone. Mounted coaxially within the dome in the negative pressure region is an electric heater ring formed by a helical resistance coil. When the heater ring is energized, the air circulating in the loop passes through the coil and is raised in temperature to a level that is a function of fan velocity, the higher the velocity the lower the temperature level.

4 Claims, 2 Drawing Sheets

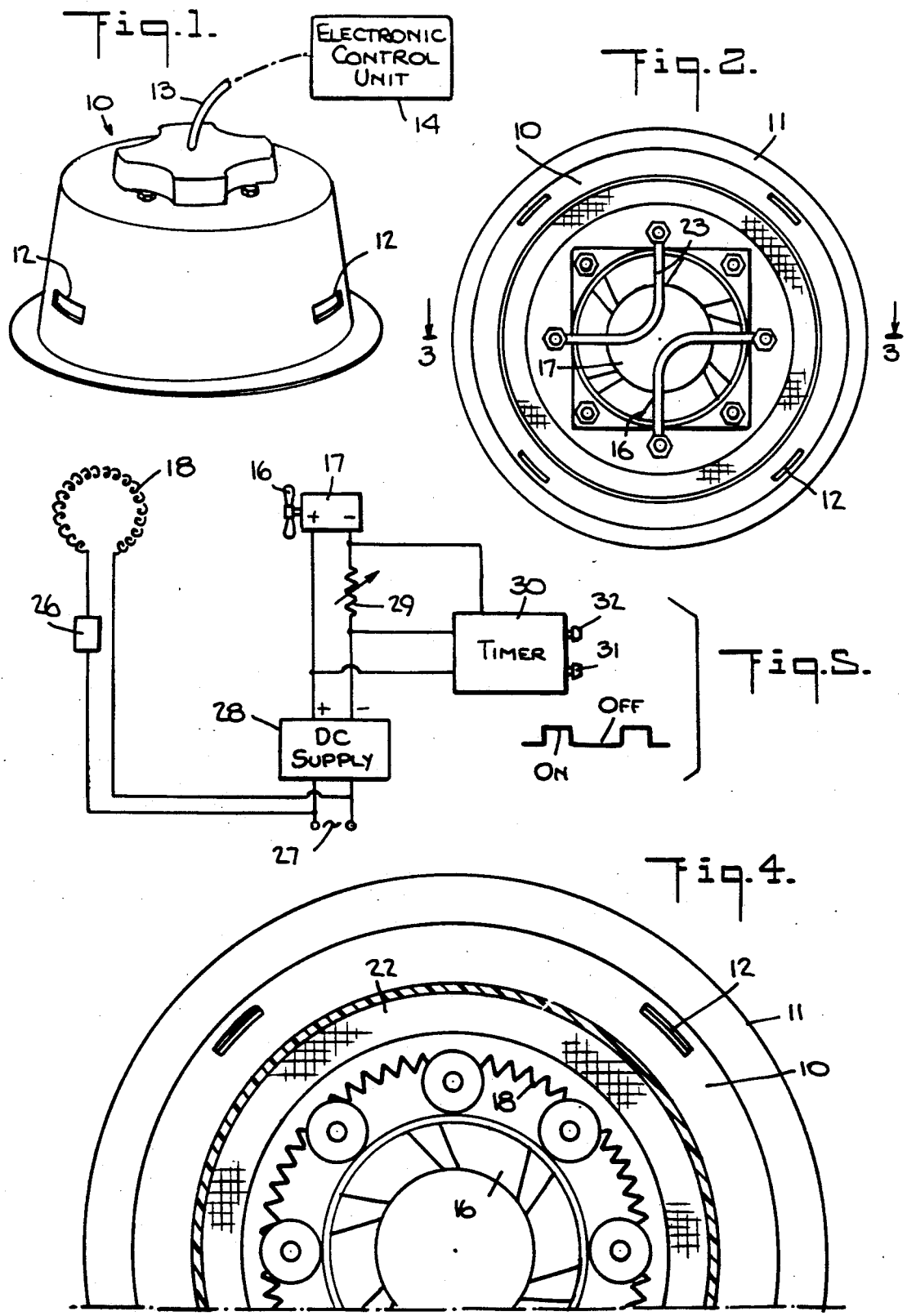

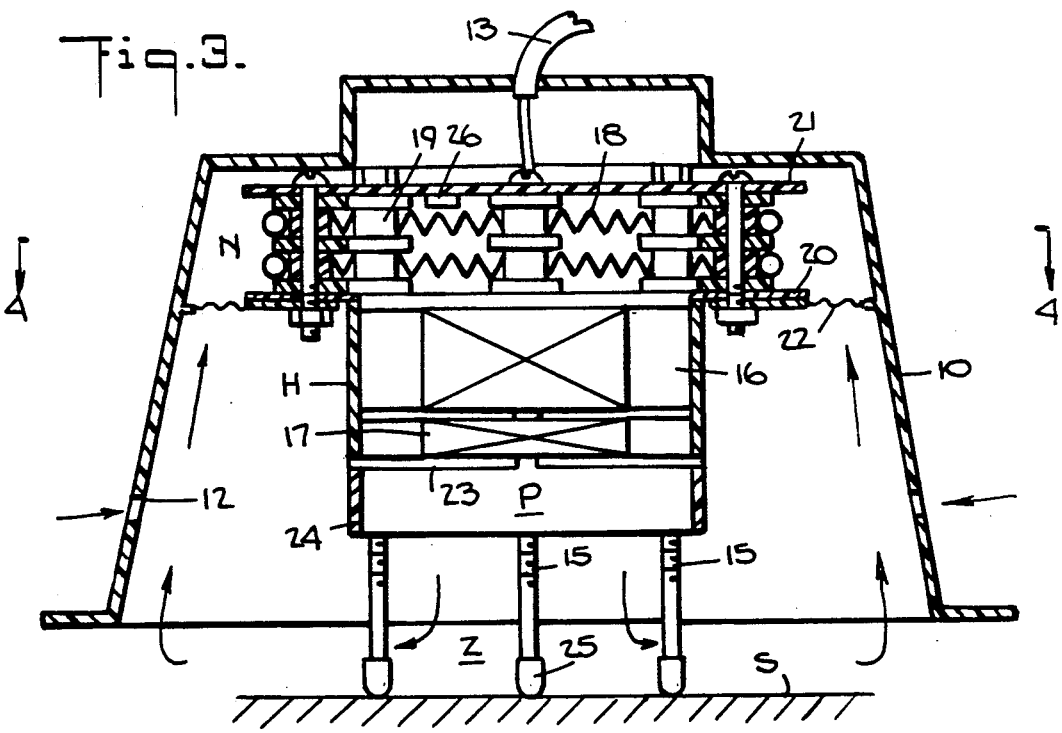
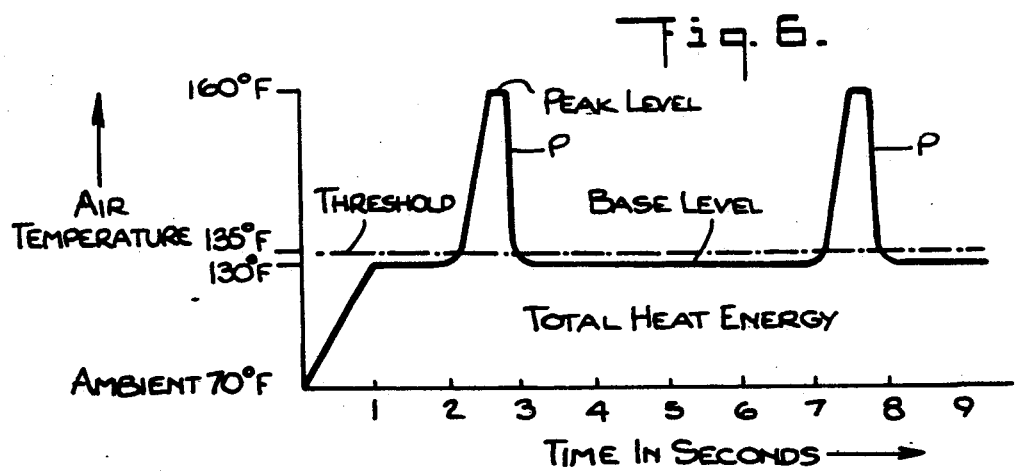
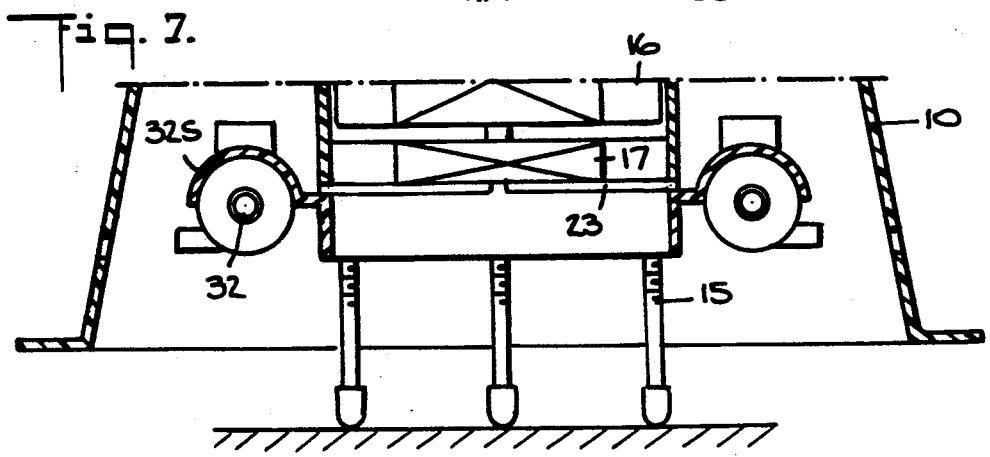

UNIVERSAL THERMOTHERAPY APPLICATOR

RELATED APPLICATION

This application is a continuation of our pending application Ser. No. 667,186, filed Mar. 11, 1991, now U.S. Pat. No. 5,107,832, granted Apr. 28, 1992 entitled "Universal Thermotherapy Technique," whose entire disclosure is incorporated herein by reference.

BACKGROUND OF INVENTION

1. Field of Invention

This invention relates generally to thermotherapy, and more particularly to a universal applicator for domestic, professional or field use adapted to apply therapeutic heat to a localized skin surface of a patient whose threshold of sensitivity is determined by that temperature level of the heating medium to which the patient is exposed, above which the patient experiences discomfort or injury, the applicator subjecting the patient to periodic heat energy pulses having a peak temperature well above the temperature sensitivity of the patient, heat transfer taking place internally in the patient in the intervals between these pulses to an extent preventing an excessive rise in the temperature at the skin surface.

2. Status of Prior Art

The term "problem region" as used herein refers to a tumor, a set of muscles, or any other site underlying the skin which is causing difficulty and which lends itself to thermotherapy treatment.

The interior of the human body has a normal temperature level which is usually said to be 98.6° F. But actually, in the course of each 24-hour period, the body temperature rises above or falls somewhat below this nominal value. Body temperature is determined by the relationship existing between the amount of heat internally generated, which depends on basal metabolism and the amount of heat escaping from the body. Additional heat is produced as a result of muscular activity, this being dissipated by an increase in radiation, conduction or evaporation from the skin surface and by more rapid and deep breathing.

Medical practitioners since ancient times have known that the application of heat to the body is useful in the relief of muscle soreness and various aches and pains, as well as in the treatment of certain pathological conditions. Thus the use of heat for the treatment of arthritis and other abnormalities is now commonplace. Hot water bottles and electrical heating pads are in widespread use, not merely to provide warmth, but also to afford a degree of relief or therapy for various conditions. In applying heat to the surface of the body, one may do so by convection, by direct contact with a warmed substance; that is, by conduction, or by radiating energy into the body.

Difficulty has heretofore been experienced in effectively applying heat which is electrically or otherwise generated to a patient. When transferring heat inwardly through living tissue to a problem region underlying the skin, if the heat applied to the skin surface is within a tolerable temperature range, then not enough heat energy is transferred to this site to afford beneficial effects.

As pointed out in chapter 10, "Therapeutic Heat" in the text Therapeutic Heat and Cold, edited by Justuf F. Lehmann and published in 1982 by Williams and Wilkins, it is generally accepted that heat produces desirable therapeutic effects, for it increases the extensibility of collagen tissues, it decreases joint stiffness, and it affords pain relief. Moreover, heat relieves muscular spasms, it aids in the resolution of inflammatory infiltrates, edema and exudates, and it enhances blood flow.

As indicated in the Lehmann text, superficial heat is commonly tied in with various forms of heating media such as a paraffin bath, hot air or hot water and radiant heat (infrared). For a given patient, the temperature sensitivity threshold is that temperature level of the heating medium to which the patient is exposed, above which the patient experiences undue discomfort. Thus temperature levels of the medium below the sensitivity threshold are more or less tolerable, whereas those above the threshold are effectively intolerable. If, for example, a patient being subjected to thermotherapy finds that the heat is more than he can stand and wishes the procedure discontinued, clearly the heat of the medium to which he is exposed is above his sensitivity threshold.

One must bear in mind that the temperature sensitivity threshold is determined on the basis of continuous exposure to the heating medium, for one can tolerate much higher heat levels when one is only exposed momentarily or intermittently to high temperatures.

The temperature sensitivity threshold depends on the nature of the heating medium. Thus, as noted in the Lehmann text, when the medium is hot water which is at the same temperature and is applied to the patient in the same fashion as heated paraffin which has a low heat capacity, the paraffin can be tolerated by a patient but the hot water is intolerable for it has a high specific heat and a high order of thermal conductivity.

As a consequence, with conventional heating techniques, regardless of the medium used, when the patient is continuously exposed to a heating medium which is at a substantially constant temperature level, though this level is high enough to bring about adequate heat transfer to the problem region underlying the exposed skin, then the skin temperature is usually well above the tolerable level and this may result in extreme discomfort to the patient and even to the burning of tissue.

It is also now recognized that by heating tumors to a higher temperature than the surrounding tissue, the tumor may be caused to shrink and disappear. As noted in The New York Times of Apr. 14, 1982 (section C2) in an article on modern approaches to cancer treatment, the effectiveness of heat therapy is based on the fact that cancers have poor circulation and a reduced ability to dissipate heat. "Thus a temperature of more than 113 degrees Fahrenheit could destroy cancer cells while sparing normal tissue."

In order to generally demonstrate the value of thermotherapy in the treatment of problem regions, we shall consider the backache, one of the most common of all human afflictions. As noted in the "Book of Back Care," published by the American Medical Association, most of us at some time in our lives suffer from backache.

The back, an extraordinarily complex structure, is composed of bones, cartilage, nerves, blood vessels, and layers upon layers of muscle, each with its own potential for causing trouble. In physical therapy, heat is most often used to help relax tense and spastic back muscles. As indicated in the "Book of Back Care," heat is usually applied to the skin overlying the problem region with hot towels, hot water bottles, electric heating pads, infrared lamps or paraffin baths.

Because in all conventional heat applicators, the heat is applied continuously to the skin area overlying the problem region, this imposes strict limits on the acceptable temperature level. Thus if one seeks to have the heat penetrate more deeply into the body, the temperature at the surface area must be raised to promote more rapid heat transfer, for the higher the differential between the internal and external temperatures, the greater the rate of transfer. But a point is then quickly reached at which the patient is made uncomfortable—for one can only tolerate continuously applied heat whose temperature level is not excessively above body temperature. The temperature sensitivity threshold for a given patient is that temperature level of the heating medium to which the patient is continuously exposed above which the patient experiences serious discomfort.

Because continuous heat therapy techniques, to be completely safe, must operate at a relatively low temperature level not much higher than the sensitivity threshold, they are of limited effectiveness in the treatment of backache and other painful conditions that are relieved by heat. And in the case of tumors, the practical problem encountered when applying heat thereto continuously is that the temperature necessary to raise the tumor temperature to a level destroying cancer cells cannot be tolerated at the skin surface overlying the tumor.

The concern of the present invention is not with the heat treatment of any particular medical condition or problem region, but with a more effective thermotherapy applicator therefor.

The prior Guibert U.S. Pat. No. 4,667,658 discloses a technique for applying therapeutic heat to a skin surface area of a patient whose threshold of sensitivity is determined by that temperature level of the heating medium to which the patient is continuously exposed, above which the patient experiences discomfort or injury. In this technique, the skin surface is exposed to a heating medium whose temperature is at a base level that is well above ambient but no higher than the temperature sensitivity threshold, the temperature of the medium being periodically raised above the base level to create high heat energy pulses whose peak temperatures are much higher than the threshold.

The duty cycle of these pulses is such as to allow for internal heat transfer to take place in the region below the exposed area of the patient in the intervals between pulses to an extent preventing an excessive rise in temperature at the skin surface whereby the patient gains the benefit of high heat energy treatment without discomfort or injury.

To carry out this technique, the Guibert patent discloses an instrument in which a motor-driven centrifugal air blower operated at a constant speed draws air from the atmosphere at ambient temperature and blows this air through an applicator which can be oriented to direct the hot air stream to impinge on the localized skin surface of the patient being treated, the hot air then being discharged into the atmosphere.

Mounted at the inlet of the blower motor is an electrical heater coil which acts to heat the air drawn into the blower. An electronic controller is interposed between the heater element and a high voltage supply to energize the heater with a relatively low voltage to establish the base temperature level in the pulsatory heating pattern to which the patient is subjected. The electronic controller is periodically bypassed by means of a repeat cycle timer, whereby the high voltage from the supply is then directly applied to the heater element to raise the air temperature of well above the base level to create high energy pulses whose peaks are much higher than the threshold.

In this Guibert instrument, the blower and the heater are mounted in a casing having an outlet coupled by a flow tube terminating in a universal joint on which the applicator is supported. This necessitates a stand to support the instrument, and it is not possible with this arrangement to bring the applicator to the patient and to apply the applicator to any desired skin surface area regardless of its location, for the patient must be brought to where the instrument is installed, and there are distinct limits as to where the applicator may then be applied. If, for example, it is necessary to apply thermotherapy to the legs of a horse, as a practical matter, it is impossible to do this with the instrument disclosed in the prior Guibert patent.

And while an instrument of the type disclosed in the prior Guibert patent is suitable for professional use in a physician's office or in a hospital, because of its cost, size and complexity, it does not lend itself to domestic use in the home of a patient or in the field where portability is a factor.

Also, a practical drawback of the instrument disclosed in the prior Guibert patent arises from the fact that the heated air produced by the instrument is discharged from the patient's skin into the atmosphere. Since each heater used with this instrument consumes well over 750 watts, the temperature of the air in the room or office in which the instrument is installed rises to a distinctly uncomfortable level, particularly if the instrument is being used repeatedly in the course of a day to treat patients.

Moreover, since the elevated air temperature in the room or office is being continuously drawn into the blower of the instrument and is no longer at ambient temperature, this makes it difficult to maintain constant the desired temperature levels of the thermotherapy heat pattern.

It must be borne in mind that to carry out the pulsatory thermotherapy technique effectively, it is important that the surface temperature of the skin be maintained at a base level which is below the sensitivity threshold, and if the base level temperature continues to rise, the instrument will not be effective.

The reason the instrument discloses in the prior Guibert patent requires high-wattage electric heaters is that all air fed into the heaters is at ambient temperature and at a constant air flow volume. In order to attain a desired peak temperature level which is much higher than ambient, one must provide high-wattage heaters. Such heaters and the power consumed thereby add substantially to the construction and operating costs of the instrument.

Also of prior art interest are the Guibert U.S. Pat. Nos. 4,398,535; 4,461,299 and 4,595,008.

SUMMARY OF INVENTION

In view of the foregoing, the main object of this invention is to provide a universal applicator for domestic, professional or field use adapted to apply therapeutic heat to a localized skin surface of a patient in a pulsatory heat energy pattern.

Among the significant advantages of the invention are the following:

A. The applicator is self-sufficient and includes both an air blower and heater.

B. The applicator is highly compact and may be hand-held and rested against the skin or mounted on an angularly-adjustable stand.

C. The applicator includes a relatively low wattage heater and is relatively inexpensive to construct and operate.

D. The applicator recirculates a substantial percentage of the air heated therein, and relatively little heated air is discharged into the atmosphere; hence the applicator may be used within the confines of a room or office for a prolonged period without unduly raising the room temperature.

E. The applicator may be readily applied to a skin surface at any location on the body of a patient (human or animal).

F. The applicator may be produced at relatively low cost.

Also an object of the invention is to provide an applicator capable of functioning either as a hot air or as an infrared radiation heater. In some instances, infrared radiation because of its penetrating properties may be preferably to convection heating which depends on conduction through the tissue to effect heat penetration from the skin surface to the problem region underlying the skin surface.

Briefly stated, these objects are attained in a universal applicator for applying therapeutic heat to a localized skin area of a patient. The applicator includes a casing dome whose open base is maintained in spaced relation to the skin area to define an air flow zone therebetween. Coaxially mounted at an intermediate position within the dome is a motor-driven fan which when electrically energized creates a negative pressure region in the dome above the fan and a positive pressure region therebelow, whereby air drawn from the negative pressure region is propelled into the positive pressure region from which it is discharged into the air flow zone. From this zone, the air is returned to the negative pressure region, thereby creating a circulatory flow loop minimizing the discharge of air into the atmosphere outside the flow zone.

Mounted coaxially within the dome in the negative pressure region is an electric heater ring formed by a helical resistance coil. When the heater ring is energized, the air circulating in the loop passes through the coil and is raised in temperature to a level that depends on fan velocity; the higher the velocity, the lower the temperature level. An electronic control system is associated with the fan motor to periodically change the fan velocity from a predetermined high value at which the resultant temperature level of the air in the flow zone is at a base level above ambient but no higher than the sensitivity threshold of the patient being treated, to a predetermined low value at which the resultant temperature level is raised above the base level to create high temperature heat pulses whose peaks are well above the sensitivity threshold.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of a thermotherapy applicator in accordance with the invention;

FIG. 2 is a bottom view of the applicator;

FIG. 3 is a longitudinal section taken in the plane indicated by line 3—3 in FIG. 2.

FIG. 4 is a transverse section taken in the plane indicated by line 4—4 in FIG. 3;

FIG. 5 illustrates in block diagram the electrical control system for the applicator:

FIG. 6 is a graph illustrative of the temperature pattern of heat produced by the applicator; and FIG. 7 is a section taken through another embodiment of the applicator which is capable of producing either infrared radiation or convection heating.

DESCRIPTION OF INVENTION

The Applicator

Referring now to FIGS. 1 to 2, there is shown an applicator according to the invention, the applicator including a dome-shaped casing 10 molded of high-strength, fire retardant, synthetic plastic material having electrical insulating properties., Suitable for this purpose is polycarbonate. Casing dome 10 has an open base surrounded by a circular flange 11. In practice, fitted onto this flange is an annular ring of elastomeric material which acts as a protective cushion when the applicator is applied to the skin of the patient being treated. Formed in the wall of the dome and adjacent flange 11 is a circular series of air-inlet ports 12 of pre-determined size. The applicator is coupled by a flexible cable 13 to an electrical control unit 14 which supplies operating power to the electrical heater and to the fan motor included in the applicator.

As shown in FIGS. 3 and 4, supported coaxially within casing dome 10 at an intermediate position therein by threaded mounting rods 15 is a tube axial fan 16 supported on the shaft of a miniature DC motor 17, the fan and motor being contained with a cylindrical housing H. Suitable for this purpose is a NIDEC Beta SL 12V DC tube axial fan blower manufactured by Nippon Densan Corp., this fan being disclosed in U.S. Pat. No. 4,682,065.

Coaxially mounted above fan 16 in the dome is an electric heater ring 18 formed of a helical coil of resistance wire wound about a circular array of ceramic stand off insulators 19 sandwiched between lower and upper annular insulation plates 20 and 21.

When fan motor 17 is energized, the rotating fan creates a negative pressure region N in the upper dome space occupied by heater 18, and a positive pressure region P below the fan. An annular protective screen or mesh 22 extends between the lower plate 20 and the wall of the dome to block access of foreign elements to the heater ring. A protective wire guard 23 is interposed between motor 17 and a collar 24 attached thereto which is aligned with cylindrical housing H and blocks access to the fan.

Threaded rods 15 which support the fan motor and the heater ring and the collar attached thereto extend from the roof of the dome and terminate in feet 25 of elastomeric cushioning material. These feet serve, as shown in FIG. 3, to maintain the applicator in spaced relation from the localized skin surface S of a patient to be treated, thereby creating in this relatively narrow space a turbulent air flow zone Z. Supported on the underside of annular insulation plate 21 is a heat sensor 26, preferably in the form of a bi-metallic switch, such as a Klixon switch marketed by Texas Instruments Company, to protect the applicator should it become overheated for any reason.

In operation, because of the negative pressure in region N in the dome, air is drawn from flow zone Z below the open base of the dome into this region. At the same time, some outside air is drawn into the negative pressure region N through ports 12, as indicated by the arrows in FIG. 3.

The air drawn into negative pressure region N passes through heater ring 18 and is heated thereby to a uniform temperature before being propelled by the fan into the positive pressure zone P, from which the heated air is discharged into flow zone Z where it acts to apply heat to skin surface S. From this zone, a substantial percentage of the heated air returns to the negative pressure zone, thereby creating a circulatory loop from which little heated air escapes into the atmosphere surrounding the applicator.

It is to be noted that the tube axial fan projects a column of air at a uniform temperature into the positive pressure region P, and that this column is surrounded by air drawn from flow zone Z in the positive pressure region. Because of collar 24 there is no interference therebetween.

Hence with an applicator in accordance with the invention, it becomes possible to recirculate a substantial percentage of the heated air and thereby eliminate major heat losses. And it becomes possible to pulsate the flow of air projected into air flow zone Z without pulsating the power applied to the heater element, so that this power is maintained constant during the base and peak phases of the pulsatory heat wave applied to the patient. In this way, the power required to obtain good results can be substantially reduced as compared to that required in the instruments disclosed in the prior Guibert patent. And with an applicator in accordance with the invention, the ambient temperature of the room in which the applicator is operating undergoes no significant increase, for substantially all of the heat energy generated by the applicator is exploited for purposes of thermotherapy.

Electronic control unit 14 functions to apply AC operating power (i.e., 12 volts 60 cycle AC) to electric heater ring 18 and to control this power so that the temperature of the air applied to a patient being treated can be tolerated by the patient, bearing in mind that no two patients have exactly the same threshold sensitivity and that some patients are rendered uncomfortable at temperatures which are acceptable to others. In practice, therefore, it is desirable that the control unit be capable of being adjusted to effect temperature changes in small increments.

While heater 18 is being energized, the DC fan motor 17 has an operating voltage applied thereto which changes periodically from the rated voltage of motor 17 to a lower voltage level. Thus if the rated voltage for the fan motor is 12 volts DC, at which voltage the fan then operates at high velocity, and the voltage applied to the motor changes periodically from 12 volts to 8 volts DC, then the fan velocity will go periodically from high to low.

It is important to understand the relationship between the velocity of air passing through the heater coil ring from its outer periphery to its inner periphery and the amount of heated imparted to this air by the heater.

When the fan is operating at high velocity, as a consequence of which the air passes quickly through the heater ring, then the amount of heat imparted to the air in the course of its transit through the coil will be small, resulting in a relatively low rise in air temperature. When, however, the fan is operating at low velocity and the air then passes slowly through the heater coil ring, then more heat will be imparted to the air in the course of its transit through the heater coil. This will result in a relatively high rise in air temperature.

In the applicator, when the motor operates at its rated voltage, the fan velocity is then high and the air is heated to a base level above ambient temperature but somewhat below the temperature sensitivity of the patient. When the motor operates at below its rated voltage and the fan velocity is low, the air is then heated to an elevated peak temperature level well above the base temperature level. The relationship of the base and peak temperature levels to the sensitivity threshold of a patient will now be considered in connection with the thermotherapy technique carried out by the applicator.

The Thermotherapy Technique

An applicator in accordance with the invention functions to carry out a thermotherapy technique in which heat energy is applied to a localized skin surface area of a patient overlying a problem region by an air stream passing through zone Z whose temperature in the intervals when the velocity of the air stream is high is at a substantially constant base level which is well above ambient but somewhat below the sensitivity threshold of the patient. In the intervals in which the velocity of the air stream is low, its temperature is then elevated to reach a peak level well above the base level. Thus if the temperature were maintained at this peak level for, say, a minute or more, though it would then act to promote rapid inward heat transfer to the problem region in the body, it would at the same time cause extreme discomfort and possible injury to the patient.

In order, therefore, to render the applied heat energy tolerable and at the same time bring about a rapid inward heat transfer from the skin area to the problem region, the heat energy in a technique in accordance with the invention is applied in a pulsatory thermal wave pattern.

In a technique in accordance with the invention, a stream of air is projected toward a limited skin area of the patient being treated in zone Z. As shown graphically in FIG. 6, the air temperature which is drawn from the atmosphere is initially at ambient (i.e, 70° F.). When the velocity of the air as controlled by the fan is high, then the air is heated to a constant base temperature level (i.e., 130° F.) which is well above ambient (70° F.) but somewhat below the temperature sensitivity threshold of the patient (i.e., 135° F.).

In FIG. 6, temperature is plotted against time in one second increments. It will be seen that the temperature of the air stream is periodically raised well above its base level by heat energy pulses to a peak level (i.e., 160° F.), which is much higher than the sensitivity threshold. This rise in temperature takes place when the air velocity, as controlled by the fan, is low.

In the example shown, the duty cycle is such that each pulse P, which has almost a one second duration, is followed by an interval of four seconds in which the flowing air is at its base level temperature.

The resultant pulsatory thermal air wave pattern is such that the stream of hot air at the base temperature level is blown toward the localized skin area to impinge thereon and to flow across the area in zone Z. This air stream is periodically raised in temperature to a peak level so that the localized skin area being subjected to treatment is exposed to high temperature heat energy well above the sensitivity threshold for no more than a brief period insufficient to cause discomfort, followed by an interval at the markedly lower base temperature level during which rapid heat transfer takes place through the body tissue toward the problem region. This inward transfer acts to reduce the temperature at the surface to a degree preventing a significant rise thereof above the sensitivity threshold.

A technique in accordance with this invention makes it possible to produce a much greater rise in the temperature of an internal problem region underlying a limited skin area subjected to the heat without, however, discomfort to the patient or damage to the tissue being heated. Because the internal heat is significantly higher in temperature than that heretofore obtainable without discomfort or damage, the beneficial effects are far more pronounced.

The Electronic Control Unit

FIG. 5 shows one preferred embodiment of the electronic control unit 14 which in FIG. 1 is remote from the applicator 10. The unit is connected to an AC power line 27 (i.e., 120 volts AC, 60 Hz), and it supplies this voltage through bi-metallic switch 26, which, as explained previously, acts to cut off the heater if for any reason the temperature within the applicator reaches an excessive level.

The AC power line voltage is also applied to a DC supply 28 which includes a step-down transformer and a full-wave rectifier to produce an output DC voltage whose level matches the rated voltage of the fan motor 17. Hence if the rated voltage is 12V DC, then this is the output voltage of DC supply 28. Motor 17 operates at its maximum RPM when energized at its rated voltage, and at a lower velocity when energized at a voltage below its rated voltage.

Connected in series between the output of DC supply 28 and the input terminals of fan motor 17 is a variable resistor 29 which is adjustable to produce a voltage at the input terminals of the motor which is below the rated motor voltage, say, 8 volts DC, in which event the motor when energized at the reduced voltage level will turn fan 16 at a low velocity. If the voltage is, say, 6.5 volts, the velocity will be still lower.

Also connected to the output of DC supply 28 is a repeat cycle timer 30 having control knobs 31 and 32 for independently adjusting the on-off timer and hence the duty cycle. Thus the time range may be 1 to 20 seconds for the "off" period of the timer, and 1 to 20 seconds for its "on" period.

Timer 30 is connected in shunt relation with resistor 29 so that when in the course of each cycle the timer is "on," this acts to short circuit resistor 29, as a result of which the full output of the DC supply 28 is applied to motor 27, and it then operates at its rated voltage to drive fan 16 at high velocity. When in the course of each cycle the timer is "off," then resistor 29 is not short circuited, and a reduced voltage is applied to the motor which then operates to drive the fan at low velocity.

Thus each time timer 30 is "off" and the fan turns at low velocity, the heat produced then reaches the desired peak level well above the base level. But each time timer 30 is "on," the reduced heat then produces, as a result of the high fan velocity, a base level temperature somewhat below the threshold sensitivity of the patient.

In practice the electronic control unit, instead of being remote from the applicator, may be integrated therewith.

Modified Applicator

In the applicator shown in FIGS. 1 to 4, use is made of forced convection to supply heat to the patient in a pulsatory heat pattern. In some instances, it may be desirable to subject the patient to infrared radiation in a pulsatory pattern, for such radiation penetrates tissue and is absorbed thereby and does not depend, as in the case of convection, on conduction through the tissue.

To this end, the applicator, as shown in FIG. 7, further includes an infrared heater 32 in the form of a resistance wire in a circular form which surrounds fan motor 17. Mounted above infrared heater 32 is an annular shield 32F which acts to direct infrared radiation toward the skin surface.

With the modified applicator, the associated electronic control unit will be provided with a selector switch which when the applicator is to be operated in the convection mode, then switches the unit to operate in the manner disclosed in FIG. 5. But when the applicator is to be operated in the infrared radiation mode, then the selector switch causes the unit to operate so that the infrared heater is periodically energized to provide a pulsatory heat pattern, and the fan is operated continuously to cool the skin of the patient.

Applications

An applicator in accordance with the invention can in practice be held directly or rested against a selected skin area of a human patient. Or it may be supported by means of a universal joint on an adjustable stand having pivoted arms so that the applicator may be oriented to rest against the back or shoulders of a patient should there be a need to subject these regions to thermotherapy.

The applicator is compact and portable, and the associated electronic remote control system may be housed in a small, portable cabinet, so that it is readily usable in the home as well as in a doctor's office, in a hospital or in the field. Or a pair of applicators may be provided, the applicators being so supported as to fit against opposite sides of the leg of a horse to be treated by thermotherapy.

While there has been shown and described a preferred embodiment of a universal thermotherapy applicator in accordance with the invention, it will be appreciated that many changes and modifications may be made therein without, however, departing from the essential spirit thereof.

In practice, a power controller may be interposed in the line leading to electric heater 18 so that the amount of heat generated may be adjusted to a level appropriate to a given patient. And in order to know how much heat is being generated, the applicator may be provided with a thermistor to sense the heat, the thermistor being connected to a remote digital readout.

We claim:

1. A thermotherapy technique for treating a patient having a temperature sensitivity threshold which is that temperature value above ambient at which the patient experiences undue discomfort, said technique comprising the steps of:
   (a) heating a flow zone to a temperature that is elevated well above ambient;
   (b) flowing a stream of air through said zone at a velocity which cyclically alternates between a low and a high velocity whereby heat is transferred to the air stream and the stream emerging from the zone has in each cycle a high temperature interval and a low temperature interval; and (c) exposing a skin surface of the patient to the stream emerging from the zone, the temperatures of the intervals being such that the low temperature has a base value above ambient and below the threshold, and the high temperature has a peak value much higher than the threshold, the duty cycle being such as to allow for internal heat transfer to take place in the region between the skin surface in the intervals between successive high temperature peaks to an extent preventing a significant rise in surface temperature above the threshold.

2. A technique as set forth in claim 1, wherein further includes the step of conducting the air stream from the skin surface of the patient back to the zone whereby the air stream is recirculated.

3. A technique as set forth in claim 1, wherein heat is supplied to said zone by an electrical heater operated at a substantially constant voltage.

4. A technique as set forth in claim 3, wherein said air stream is caused to flow through said zone by an electric blower operated at a voltage whose level is cyclically alternated from a low to a high voltage level.

* * * * *